(12) United States Patent
Heffron

(10) Patent No.: US 8,831,770 B2
(45) Date of Patent: Sep. 9, 2014

(54) VERTICAL MEDICATION STORAGE SYSTEM

(75) Inventor: David Heffron, San Diego, CA (US)

(73) Assignee: Carefusion 303, Inc., San Diego, CA (US)

( * ) Notice: Subject to any disclaimer, the term of this patent is extended or adjusted under 35 U.S.C. 154(b) by 1533 days.

(21) Appl. No.: 12/416,820

(22) Filed: Apr. 1, 2009

(65) Prior Publication Data

US 2010/0256800 A1  Oct. 7, 2010

(51) Int. Cl.
*G06F 7/00* (2006.01)

(52) U.S. Cl.
USPC ............................................... 700/214

(58) Field of Classification Search
USPC .................................. 700/213, 214
See application file for complete search history.

(56) References Cited

U.S. PATENT DOCUMENTS

| | | | |
|---|---|---|---|
| 5,172,829 A * | 12/1992 | Dellicker, Jr. | 221/13 |
| 5,905,653 A | 5/1999 | Higham | |
| 6,349,999 B1 | 2/2002 | Takahashi | |
| 7,630,791 B2 | 12/2009 | Nguyen | |
| 7,857,161 B2 * | 12/2010 | Pinney et al. | 221/10 |
| 2004/0182878 A1 | 9/2004 | Ho | |
| 2007/0235397 A1 | 10/2007 | Wannop | |

FOREIGN PATENT DOCUMENTS

| | | |
|---|---|---|
| CN | 2642133 | 9/2004 |
| EP | 1473228 | 11/2004 |
| WO | WO9905943 | 2/1999 |

OTHER PUBLICATIONS

International Search Report from related PCT Application No. PCT/US2010/029461 dated Mar. 31, 2010.

* cited by examiner

*Primary Examiner* — Ramya Burgess
(74) *Attorney, Agent, or Firm* — McDermott Will & Emery LLP

(57) ABSTRACT

Storage systems for inventory control are disclosed. The storage systems includes a vertical storage structure having a plurality of vertically-stacked pockets. Each vertically-stacked pocket can be configured to be separately openable for providing user access to contents of the vertically-stacked pocket. The vertical storage structure can be a vertical sliding-type door, a hinged-type door, or a wall-mounted cabinet.

30 Claims, 8 Drawing Sheets

VERTICAL MEDICATION STORAGE SYSTEM

FIELD

The present disclosure relates to inventory management systems, and, in particular, to medication storage systems.

BACKGROUND

Storage systems typically provide drawers and dispensing pockets within the drawers to store contents of interest. In medical fields, for example, storages systems are designed to provide medical supplies, including medications, at locations such as nursing stations in hospitals. By maintaining an inventory of supplies at such locations, these storage systems seek to reduce the number of trips for nurses or pharmacy personnel between the nursing station and the pharmacy to acquire the supplies, as re-stocking of the station can occur in batches. Many of these systems include access control to limit access to the supplies, thereby securing control of inventory and enhancing the management and restocking of inventory.

Existing medical storage systems utilize horizontally mounted drawers in which pockets are available for the user to access medications. One significant disadvantage with these devices is that the cabinet height, hence the storage and dispensing capacity for a given footprint, is limited by the ability of the user to look down into a pocket to retrieve the contents. In order to accurately retrieve a desired item, a caregiver needs to be able to view into the drawer. The higher the drawer, the more difficult it is to view the drawer contents.

SUMMARY

Embodiments described herein address the foregoing problem by providing a vertical storage system having a plurality of separately-openable vertically-stacked pockets.

Certain embodiments provide a storage system for inventory control. The storage system comprises a cabinet. The storage system further comprises a vertical drawer movably coupled to the cabinet and configured to move between a first position and a second position. The vertical drawer has a plurality of vertically-stacked pockets. Each vertically-stacked pocket is configured to be separately openable for providing user access to contents of the vertically-stacked pocket.

Certain embodiments provide a storage system for inventory control. The storage system comprises a cabinet. The storage system further comprises a door movably coupled to the cabinet and configured to move between a closed position and an open position, the door having an inside surface and an outside surface. The door has a plurality of vertically-stacked pockets coupled to the inside surface of the door. Each vertically-stacked pocket is configured to be separately openable for providing user access to contents of the vertically-stacked pocket.

Certain embodiments provide a storage system for inventory control. The storage system comprises a cabinet configured for wall mounting and having a plurality of vertically-stacked pockets. The storage system further comprises a plurality of electronically-controlled and individually-actuated locking devices to provide separately controlled accesses to at least some of the pockets.

It is to be understood that both the foregoing summary and the following detailed description are exemplary and explanatory and are intended to provide further explanation of the embodiments as claimed.

BRIEF DESCRIPTION OF THE DRAWINGS

The accompanying drawings, which are included to provide further understanding of the invention and are incorporated in and constitute a part of this specification, illustrate disclosed embodiments and together with the description serve to explain the principles of the disclosed embodiments.

DETAILED DESCRIPTION

In the following detailed description, numerous specific details are set forth to provide a full understanding of the disclosed and claimed embodiments. It will be apparent, however, to one ordinarily skilled in the art that the embodiments may be practiced without some of these specific details. In other instances, well-known structures and techniques have not been shown in detail to avoid unnecessarily obscuring the disclosure.

The word "exemplary" is used herein to mean "serving as an example, instance, or illustration." Any embodiment or design described herein as "exemplary" is not necessarily to be construed as preferred or advantageous over other embodiments or designs.

Various embodiments of the present disclosure address and solve problems associated with conventional storage systems (e.g., for medications) which utilize horizontal mounted drawers having pockets disposed therein for storing contents. The embodiments of the present disclosure provide a vertical storage system comprising a plurality of separately-openable vertically-stacked pockets for providing user access to contents therein. The vertical arrangement provides a smaller cabinet footprint that allows increased storage capacity for small pockets. The separately-openable pockets provide separately controlled user accesses to the contents of the pockets. This is important for contents such as medications for which an accidental mix-up of contents can have serious consequences.

Figure 1:
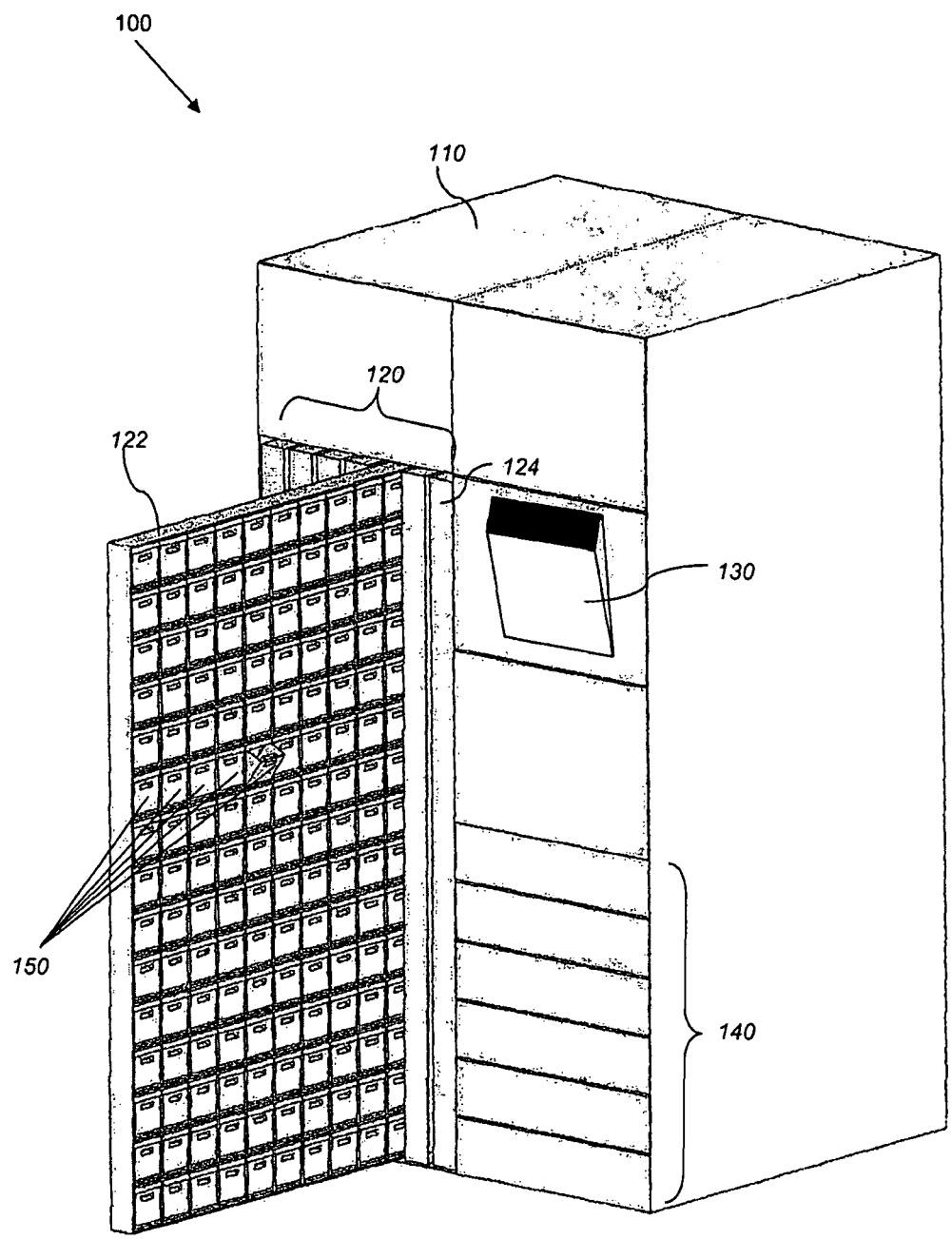
FIG. 1 is a perspective view of an exemplary storage system comprising a vertical sliding-type door having a plurality of separately-openable vertically-stacked pockets.

FIG. 1 is a perspective view of an exemplary storage system 100 comprising a vertical sliding-type drawer having a plurality of separately-openable vertically-stacked pockets. In the illustrated example, the storage system 100 includes a cabinet 110, and a plurality of vertical sliding-type drawers 120 including drawer 122 and drawer 124. As the drawer 122 illustrates, each of the vertical drawers 120 includes a plurality of separately-openable vertically-stacked pockets 150 for storing contents (e.g., medications). Each of the vertical drawers 120 can be individually moved (e.g., slid) in and out of the cabinet 110 between a first position and a second position and positions therebetween. For example, the vertical drawer can be fully within the cabinet 110 with no pockets exposed in the first position (see door 124), or at least partially outside the cabinet with some of the pockets exposed in the second position (see door 122). The vertical sliding-type drawers 120 can be mounted on or suspended from tracks (not shown) and provided with wheels or bearings to facilitate the movement between the first and second positions.

The cabinet 110 can optionally include horizontally mounted drawers 140 and shelves (not shown) for storing additional contents. The separately-openable and vertically-stacked pockets in each of the vertical drawers 120 can be equipped with electronically-controlled and individually-actuated locking devices for providing controlled access of the contents of the pockets. Various possible features and arrangements of the vertically-stacked pockets and the electronically-controlled and individually-actuated locking devices are described below with respect to FIGS. 2-4. For user-interaction (e.g., user-selection of contents), the cabinet 110 can include a user-interface 130 such as a touch screen display. In some embodiments, the user interface 130 is an integrated computer system having a processor and a touch screen display in the same package. The processor can perform at least some of the user-authentication and inventory control functions described above. The storage system 100 may be optionally provided with additional devices such as an ID input module and a lock control to be described below with respect to FIG. 4. Upon authentication, the appropriate vertical drawer 120 can be indicated to the user to pull open the vertical drawer 120 to the second position. Alternatively, embodiments of the cabinet 110 can cause the vertical drawer 120 to extend automatically from the first position.

Figure 2:
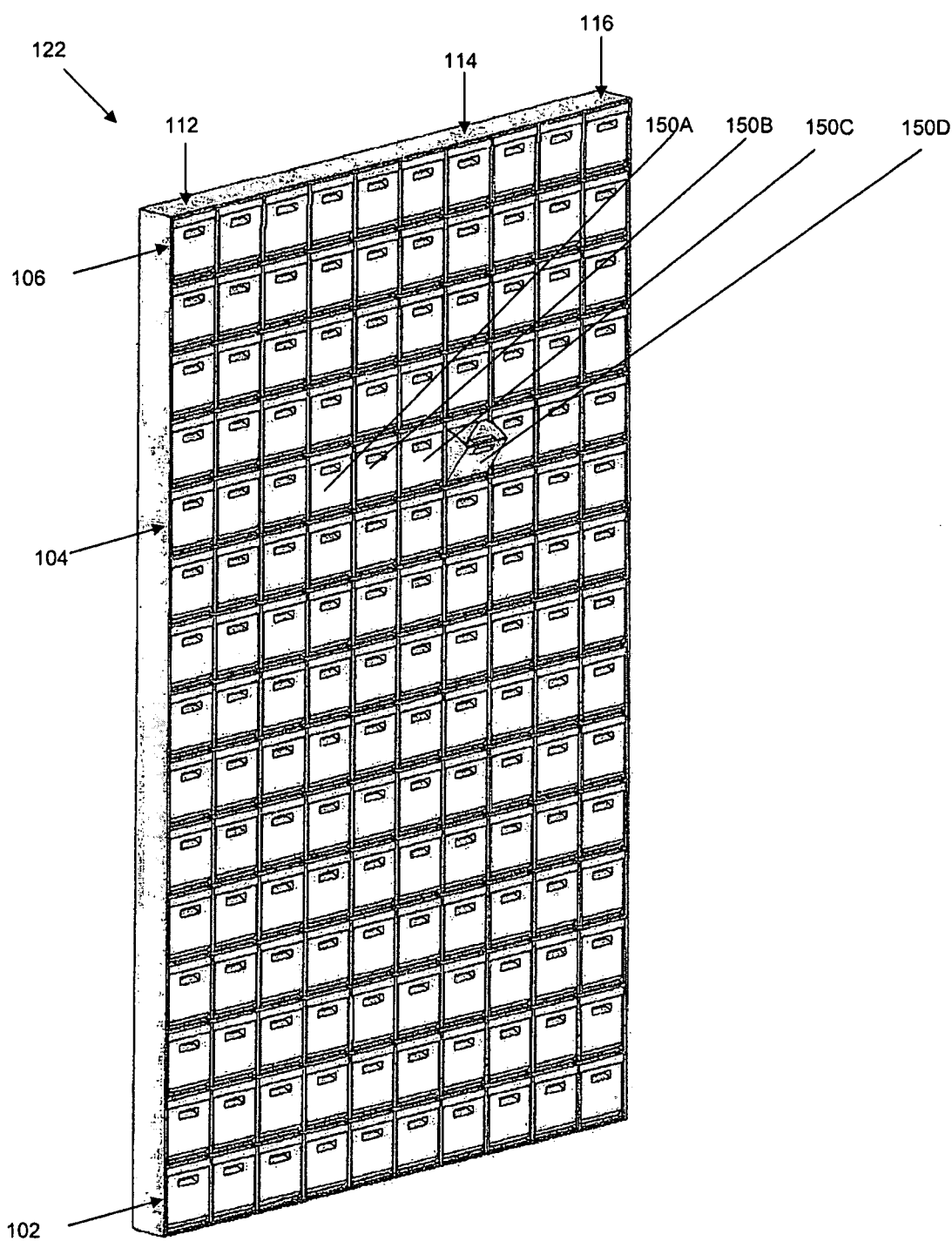
FIG. 2 is a perspective view of a vertical sliding-type door having a plurality of separately-openable vertically-stacked pockets according to certain embodiments.

FIG. 2 is a perspective view of the vertically-stacked doors 122 having the plurality of separately-openable vertically-stacked pockets. As shown in FIG. 2, the vertically-stacked pockets can be aligned along rows such as a bottom row 102, an intermediate row 106, and a top row 106. The vertically-stacked pockets can also be aligned along columns such as a left-most column 112, an intermediate column 114, and a right-most column 116. The row 104, for example, includes pockets 150A, B, C, D. Each of the pockets 150A-D is separately openable as shown with the pocket 150D to provide user access to contents (e.g., medications) stored in the pocket 150D. Due to the vertical arrangement of the storage structure, the top row 106 can be disposed at an eye level of an average user. By contrast, the top horizontally mounted drawer in a conventional storage system can be disposed roughly at a chest level of an average user if a full viewing of the contents placed in pockets is to be provided. The difference results in increased storage capacity for a given footprint for vertical storage systems of the present disclosure.

While all of the vertically-stacked pockets of the exemplary vertical drawer 122 shown in FIG. 2 are of the same size, the pockets may be of different sizes. For example, in certain embodiments, some pockets (not shown) may have a width spanning two or more columns and/or a height spanning two or more rows. In some embodiments, the pockets may also be modular in the sense that they can be removed and replaced with other pockets as will be described in more detail later. In those embodiments in which there are different sizes of modular pockets, the vertical drawer 122 can be reconfigured by repositioning some of the removable pockets. For example, assume that initially the vertical drawer 122 includes at least one large (two-columns wide/one-row high) pocket located in the bottom row 102 and two small (one-column wide/one-row high) pockets in the top row 106. After determining that the large pocket is more useful in the top row 106, the vertical drawer 122 can be reconfigured by removing the two small pockets from the top row 106 and the one large pocket from the bottom row 102 and exchanging their locations.

Figure 3A:
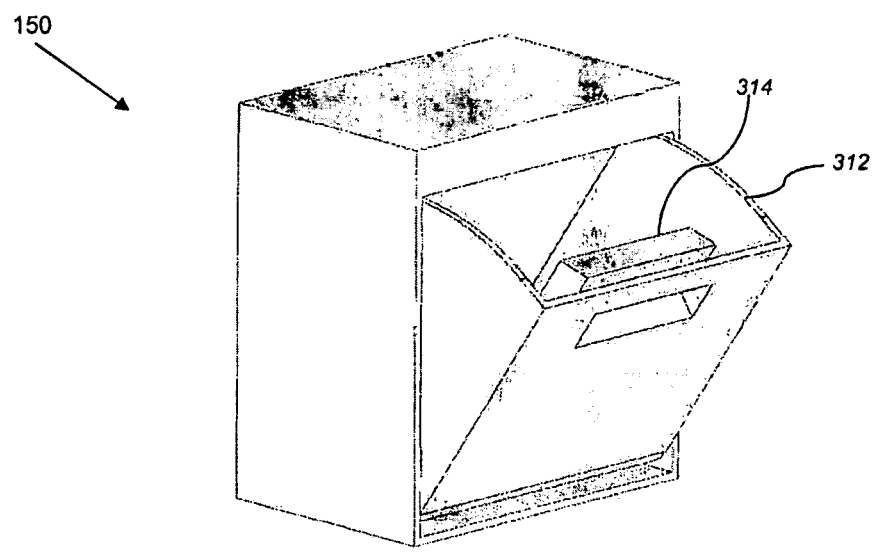
FIG. 3A is a first perspective view of an exemplary modular pocket that can be employed as one of the vertically-stacked pockets.
Figure 3B:
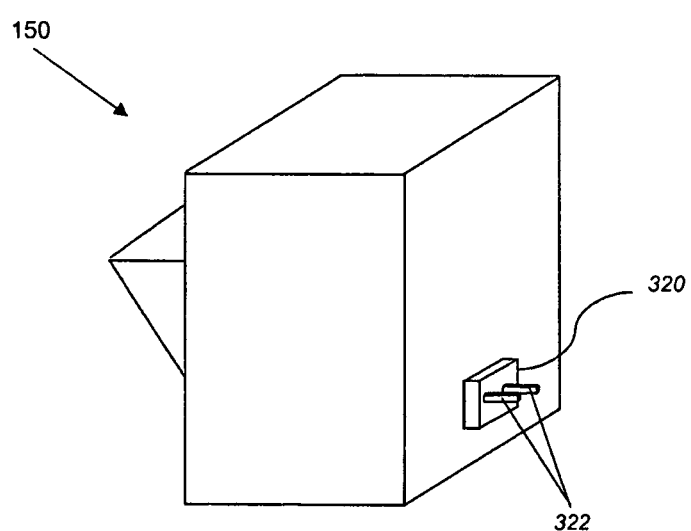
FIG. 3B is a second perspective view of the exemplary modular pocket of FIG. 3A.

FIG. 3A is a first, front perspective view of an exemplary modular pocket 150 that can be used as one or more of the vertically-stacked and separately-openable pockets such as those shown in FIG. 1. In the illustrated example, the pocket 150 is a tilt-out bin having a tiltable container 312 for storing contents such as medications. The tiltable container 312 can have a lock 214 to separately lock the container 312 in a closed and locked-position when not in use. FIG. 3B is a second, rear perspective view of the exemplary modular pocket 150. In the illustrated example, the pocket 150 includes an exemplary embodiment of a pluggable adapter 320 having prongs 322. When the modular pocket 150 is placed into a frame of a vertical door, the prongs 322 are plugged into female receptacles disposed in the frame. The prong-receptacle joint made thereby allows the modular pocket 150 to be securely held by the frame. Additionally, if the modular pocket 150 is equipped with an electronically-controlled locking device, the prongs 322 can also serve as electrical terminals to provide electric power to the locking device. Such an electronically-controlled locking device and operation thereof will be described in detail below. The pocket embodiments described above are exemplary only, as other pocket embodiments may be employed without departing from the scope this disclosure.

Figure 4:
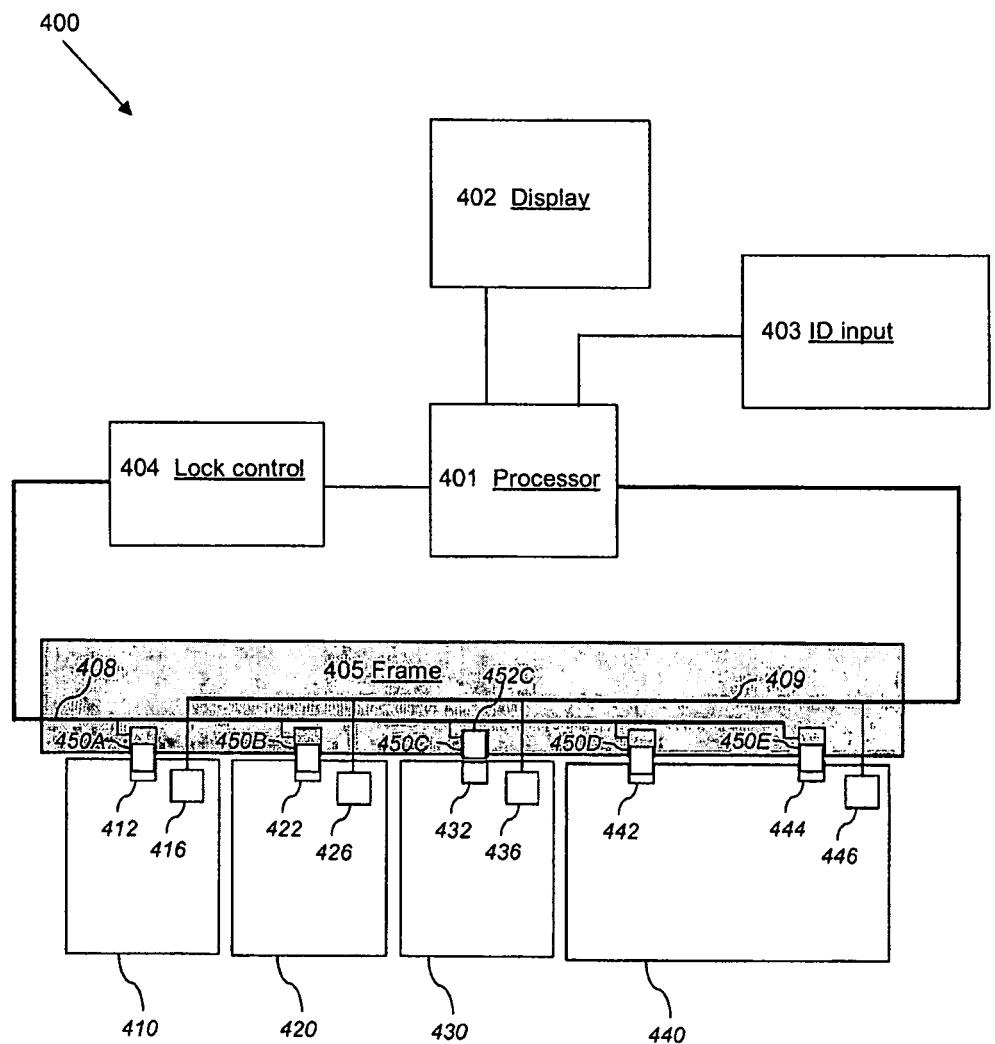
FIG. 4 is a schematic block diagram illustrating an exemplary control system for providing controlled access and inventory control of contents of vertically-stacked pockets according certain embodiments.

FIG. 4 is a schematic block diagram for illustrating an exemplary control system 400 for providing controlled access and inventory control of contents of separately-openable vertically-stacked pockets according certain embodiments. The control system 400 includes a processor 401, a display 402, an ID input module 403, and a lock control 404 in data communication with the processor 401. FIG. 4 also depicts a portion of a row of vertically-stacked pockets 410, 420, 430, 440, and a frame portion 405 disposed above the row of pockets. The display 402 may be a touch screen display allowing a user to select contents via, e.g., buttons and other controls shown on the screen.

In the illustrated example, the frame portion 405 comprises locking devices 450A-E that are in data communication with the lock control 404 via a lock control bus 308 and configured to provide controlled user accesses to contents of the pockets 410, 420, 430, 440. The locking devices 450A-E are electronically-controlled and individually-actuated locking devices. The locking devices 450A-E can include actuators based on solenoids, magnets, or motors to actuate a lock by either supplying or removing electrical power. By way of example, actuators (e.g., electro-magnets or solenoids) can be mounted on the frame portion 405 and corresponding locks (e.g., armatures for the electro-magnets or solenoids) can move between the actuators and slots 412, 422, 432, 442 provided in the pockets 410, 420, 430, 440. When an actuator associated with a particular pocket is energized (e.g., powered), the corresponding lock is pulled up by the actuator, thereby locking the pocket and prohibiting user access to the contents of the pocket. On the other hand, when the actuator is de-energized (e.g., not powered), the corresponding lock is biased downward (e.g., by a spring) within the slot, thereby unlocking the pocket and providing user access to the contents of the pocket.

Alternatively, the actuators are mounted in each of the pockets, and the corresponding slots can be provided in the frame portion. In some embodiments, the pockets are locked when the actuators are de-energized and unlocked when the actuators are energized, thus providing an increased security in the event of a power-failure. In other embodiments, the locking devices are based on shape memory alloys (SMAs), also known as a "muscle wire," in lieu of actuators. A SMA "remembers" its shape and can be returned to that shape after being deformed. Non-limiting examples of SMAs include copper-zinc-aluminum-nickel, copper-aluminum-nickel, and nickel-titanium (NiT) alloys. By way of example, a lock portion of the locking device can be made from a SMA. When the SMA is not energized, the shape of the SMA (hence, the lock made therefrom) is in an un-deformed (e.g., straight) state corresponding to a locked state for the pocket. On the other hand, when the SMA is energized (e.g., heated by an electrical current), the shape of the SMA changes to a deformed (e.g., curved) state corresponding to an unlocked state for the pocket.

The control system 400 may also include a memory arrangement configured to store information about contents of vertically-stacked pockets. In the illustrated example, the memory arrangement is provided by separate memories 416, 426, 436, 446, each of which is respectively disposed in one of the vertically-stacked pockets 410, 420, 430, 440. The memories are in data communication with the processor 401 via a memory bus 409 and configured to store information about the contents of respective vertically-stacked pockets. Alternatively, a central memory (not shown) may be employed in lieu of or in conjunction with the separate memories.

Initially, when a storage system is not in use, the processor 401, depending on a specific design for the locking devices, energizes or de-energizes the actuators or SMAs associated with different locking devices to place all of the pockets in locked states. The processor 401 waits for an indication from a user-interface device, such as the touch screen display 402, that a user (e.g., a nurse or other care provider) has made a request for a medication or other supplies, which will be contained in one or more vertically-stacked pockets. The user can make one or more supply selections and send the corresponding request for the supplies via the touch screen display 402 or any other suitable input devices such as a mouse, a touchpad, or a bar-code scanner.

In certain embodiments, the processor 401 may require completion of user-authentication before providing the requested access to a pocket that contains the requested supplies. In some of such embodiments, user-authentication involves the user inputting a password on the touch screen display 402 and the processor 401 verifying the input password against a list of passwords of authorized users. Alternatively, the user-authentication may involve the user providing ID information via the ID input module 403. For example, in certain embodiments, the ID input module 403 is a scanner device that is configured to read a barcode on the user's ID tag. The processor 401 after receiving the barcode information verifies the information against a stored list of authorized users. Alternatively, the ID input module 403 may be a device configured to measure biometric characteristics of the user. Non-limiting examples of biometric characteristics include fingerprint, face recognition, hand and palm geometry, iris recognition, signature verification, and voice/speech recognition. In those embodiments based on a biometric measurement, the processor 401 is configured to receive data indicative of biometric characteristics from the ID module 303 and verify the measured biometric characteristics against stored biometric characteristics of authorized users. The user-identification embodiments described above are exemplary only, as other embodiments of user-authentication can be employed without departing from the scope of this disclosure.

After successful completion of the user authentication, the processor 401 can determine a location (e.g., row-column address) of the pocket containing the requested supplies based on information about contents received from the memory arrangement such as the memories 416, 426, 436, 446. Such content information may be gathered by the processor 401 periodically or after each user interaction to update a record or database of the content information. The processor 401 then provides data indicative of the pocket location to the lock control 404. The lock control 404 then provides an energizing (or de-energizing) signal (e.g., an electrical current) to an actuator or SMA of the locking device associated with the pocket, thereby unlocking the pocket. A door or a container of the pocket may be spring-loaded such that when the pocket is unlocked, the door or the container opens automatically forward. Alternatively, an indicator at the appropriate pocket may be provided to indicate to the user which pocket contains the supplies, and the user is then able to open the pocket. The lock control 404 may include a bank of semiconductor or electromechanical switches that are interfaced to the processor 401 via a multiplexer and electrically connected to the actuators or SMAs of the locking devices associated with the vertically-stacked pockets 410-440.

While all connections are wired connections in the particular embodiments shown in FIG. 4, in alternative embodiments, some or all of the connections may be wireless (e.g., RF links). By way of example, the processor 401 may gather content information from the memories 416, 426, 436, 446 via a wireless communication link (e.g., WLAN), rather than via the memory bus 409. By way of another example, the ID input device 403 may communicate ID information (e.g., biometric characteristics) to the processor 401 wirelessly.

After the user removes the contents of the unlocked pocket, the user may be required to indicate the number of supplies that he or she has taken so that the processor 401 can update the pocket content information in the record or database. This can be achieved, for example, by the user pushing a "take" button (provided on the pocket or elsewhere in the storage system) a number of times. Alternatively, the user can input the number on the touch screen display 402, or the system can assume that the entire contents of a pocket is taken when accessed. The update of the content information is part of an inventory control function that can be performed by the processor 401. The inventory control may include the processor 401 maintaining a record of contents of all or some of the vertically-stacked pockets, and providing the record to a central server in a hospital, for example, which may use the information to place an order for one or more depleted medications.

It shall be appreciated by those skilled in the art in view of the present disclosure that the examples shown in FIGS. 2-4 are provided for illustration purposes only, and should not be taken as limiting. For instance, some of the features of the illustrated examples can be mixed and matched. For example, locking devices associated with some pockets in a given vertical storage system may be electronically-controlled while locking devices associated with other pockets in the system are manually-operated. Some pockets in the system may be opened or closed individually, while other pockets (e.g., a row of pockets) in the system may be opened and closed as a group. Some locking devices (e.g., solenoids) in the system may be disposed within some pockets, while other locking devices in the system may be disposed outside other pockets (e.g., in a frame portion). Some memories for storing contents of the pockets in the system may be disposed inside some pockets, while one or more other memories in the system are disposed separately from the pockets. Some or all of the memories may be resident in the processor 401 itself. The processor 401 may require user-authentication before allowing the user to make content selections. The inventory control may be performed by another processor on a network.

Figure 5A:
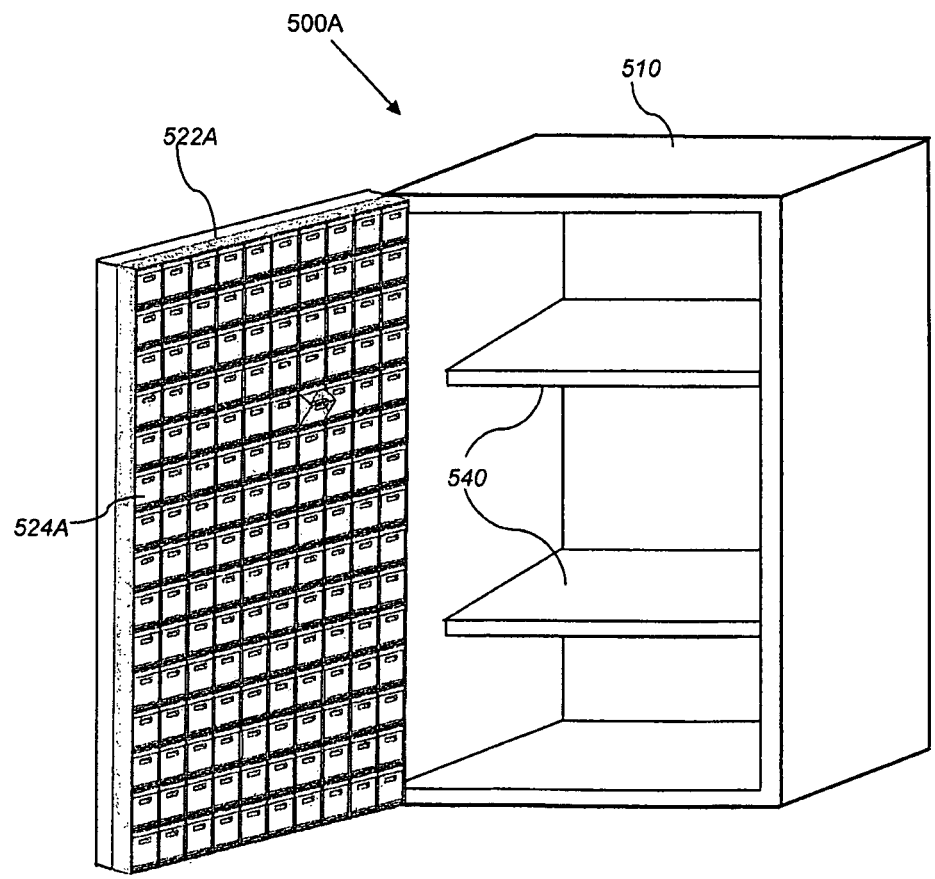
FIG. 5A is a perspective front view of an exemplary storage system comprising a hinged-type door having a plurality of separately-openable vertically-stacked pockets.

FIG. 5A is a perspective view of an exemplary storage system 500A comprising a hinged-type door having a plurality of separately-openable and vertically-stacked pockets. In the illustrated example, the storage system 500A includes a cabinet 510, and a hinged-type door 522A having a plurality of vertically-stacked pockets 524A for storing contents (e.g., medications) coupled to the inside surface of the door 522A. The cabinet 510 may be provided with one or more shelves 540 or one or more drawers (not shown) for storing additional contents. In certain embodiments, the separately-openable and vertically-stacked pockets 524A coupled to the inside surface of the door 522A are equipped with electronically-controlled and individually-actuated locking devices for providing controlled access of the contents of the pockets, as in the embodiments described in FIGS. 2-4. Although the storage system shown in FIG. 5A has only one hinged-type door having the plurality of separately-openable and vertically-stacked pockets, in alternative embodiments, the storage system may have two such doors that can be independently opened. In some embodiments, the pockets may be disposed on the outside surface of the door instead of the inside surface. Various exemplary features and arrangements of the vertically-stacked pockets and the electronically-controlled and individually-actuated locking devices are described above with respect to FIGS. 2-4, and are not repeated here. For user-interaction (e.g., user-selection of contents), the cabinet 510 can include a user-interface (not shown) such as a touch screen display mounted on the outside surface of the door 522A, or elsewhere. In some embodiments, the user interface is an integrated computer system having a processor and a touch screen display in the same package. The processor can perform at least some or all of the user-authentication and inventory control functions described earlier. The storage system 500A is provided with additional devices such as the ID input module 403 and the lock control 404 shown in and described with respect to FIG. 4, in certain embodiments.

Figure 5B:
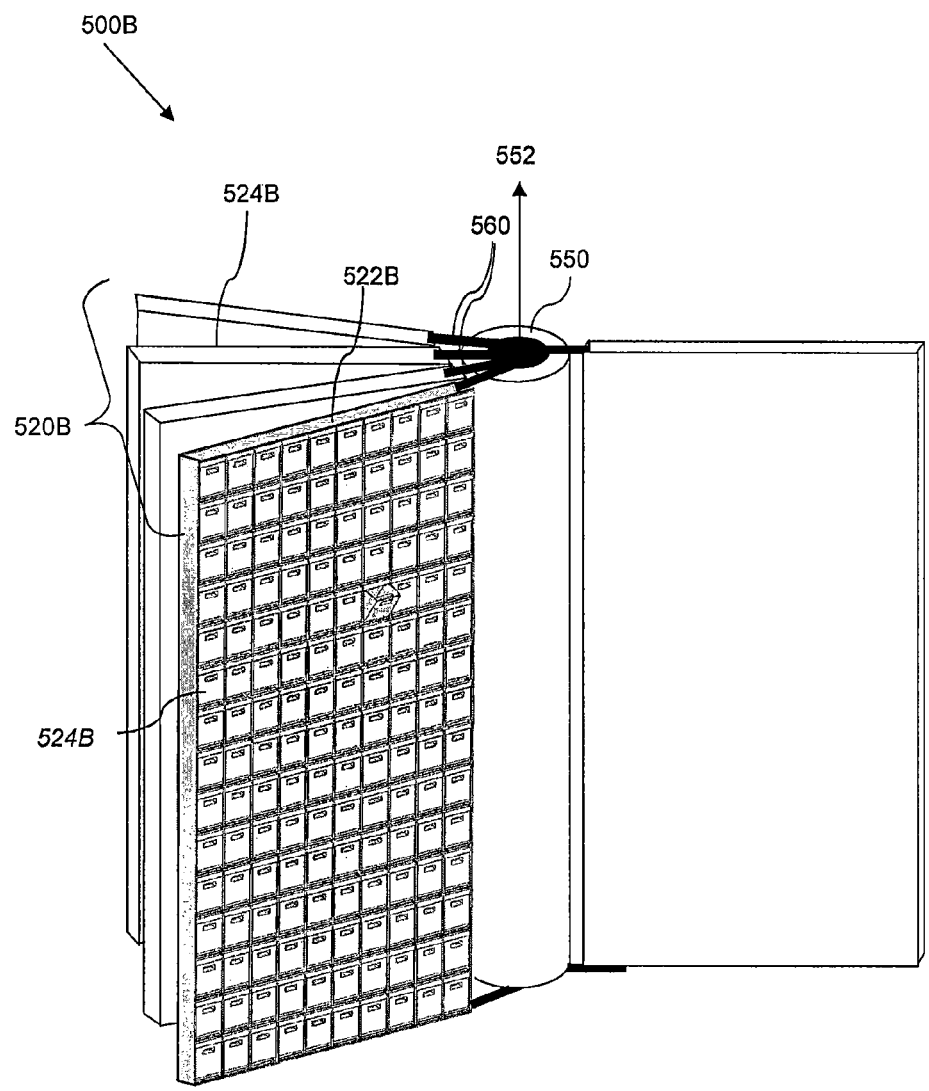
FIG. 5B is a perspective view of an exemplary storage system comprising a plurality of pivotably-mounted doors.

FIG. 5B is a perspective view of an exemplary storage system 500B comprising a plurality of pivotably-mounted doors, each pivotably-mounted door having a plurality of separately-openable and vertically-stacked pockets. In the illustrated example, the storage system 500B includes a vertical support 550 and a plurality of doors 520B pivotably mounted to the vertical support 550 via brackets 560. Each pivotably-mounted door, such as door 524B, has a plurality of separately-openable vertically-stacked pockets 524B for storing contents (e.g., medications) coupled to inside or outside or both surfaces of the door 522B. Each door is mounted so as to be pivotable about a vertical axis 552 of the vertical support 550. Each pivotably-mounted door 522B can be moved between a first position and a second position in a rotational motion. In the first position, the pockets are not fully exposed to or accessible to the user as illustrated by door 524B, whereas in the second position, the pockets 524B are fully exposed to and accessible to the user as illustrated by door 522B. It should be noted that the pivotable arrangement of the vertical doors 520B shown in FIG. 5B is exemplary only, and other arrangements can be employed without departing from the scope of this disclosure. For example, the doors 520B can be pivotably mounted on a frame attached to a wall and/or a ceiling. In some embodiments, the doors 520B may be motorized such that a door having selected supplies can be rotatably presented to the user. In yet other embodiments, the plurality of doors are slidably-mounted rather than pivotably-mounted such that the doors can be moved or slid sideways (e.g., perpendicular to the side plane of the door) from a first (e.g., unexposed) position to a second (e.g., exposed) position in a linear translational motion.

In certain embodiments, the separately-openable and vertically-stacked pockets 524B coupled to a surface of the door 520B are equipped with electronically-controlled and individually-actuated locking devices for providing controlled access of the contents of the pockets, as in the embodiments described in FIGS. 2-4. Various exemplary features and arrangements of the vertically-stacked pockets and the electronically-controlled and individually-actuated locking devices are described above with respect to FIGS. 2-4, and are not repeated here. In certain embodiments, the storage system 500B may be disposed inside an enclosure, e.g., a cabinet, (not shown) having doors or covers for additional protection of the contents. For user-interaction (e.g., user-selection of contents), such an enclosure can include a user-interface (not shown) such as a touch screen display mounted on the door of the enclosure, or elsewhere. In some embodiments, the user interface is an integrated computer system having a processor and a touch screen display in the same package. The processor can perform at least some or all of the user-authentication and inventory control functions described earlier. The storage system 500B is provided with additional devices such as the ID input module 403 and the lock control 404 shown in and described with respect to FIG. 4, in certain embodiments.

Figure 6:
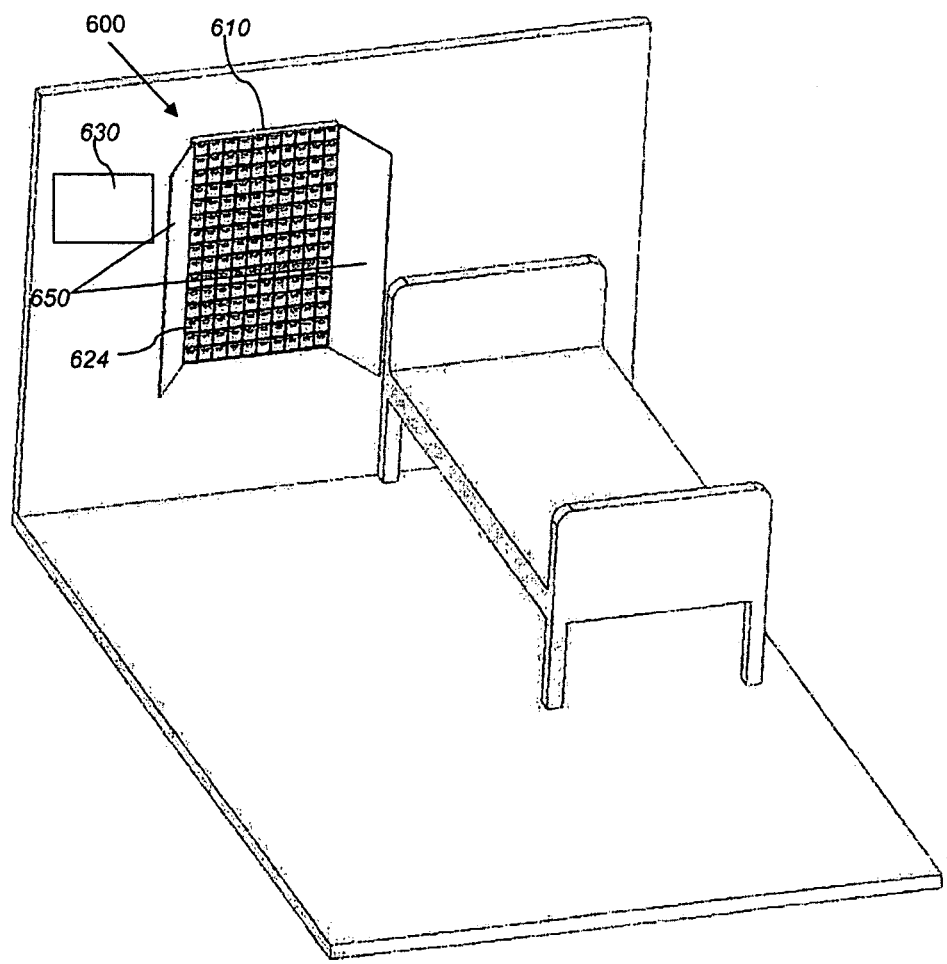
FIG. 6 is a perspective rear view of an exemplary storage system comprising a wall-mounted structure having a plurality of separately-openable vertically-stacked pockets.

FIG. 6 is a perspective view of an exemplary storage system 600 comprising a wall-mounted structure having a plurality of separately-openable vertically-stacked pockets 624. In the illustrated example, the storage system 600 includes a cabinet 610 having a plurality of separately-openable vertically-stacked pockets 624 coupled to the cabinet 610. The cabinet 610 may include one or more lockable doors or covers 650 for additional security. The separately-openable vertically-stacked pockets 624 disposed in the cabinet 610 are equipped with electronically-controlled and individually-actuated locking devices for providing controlled access of the contents of the pockets 624, in certain embodiments. Various exemplary features and arrangements of the vertically-stacked pockets and the electronically-controlled and individually-actuated locking devices are described above with respect to FIGS. 2-4, and are not repeated here. For user-interaction (e.g., user-selection of contents), a user-interface 630 such as a touch screen display may be mounted on a wall near the cabinet 610, on the outside surface of one of the doors 650, or elsewhere. In some embodiments, the user interface 630 is an integrated computer system having a processor and a touch screen display in the same package. The processor can perform at least some or all of the user-authentication and inventory control functions described above. The storage system 600 is provided with additional devices such as the ID input module 403 and the lock control 404 shown in and described with respect to FIG. 4, in certain embodiments.

Figure 7:
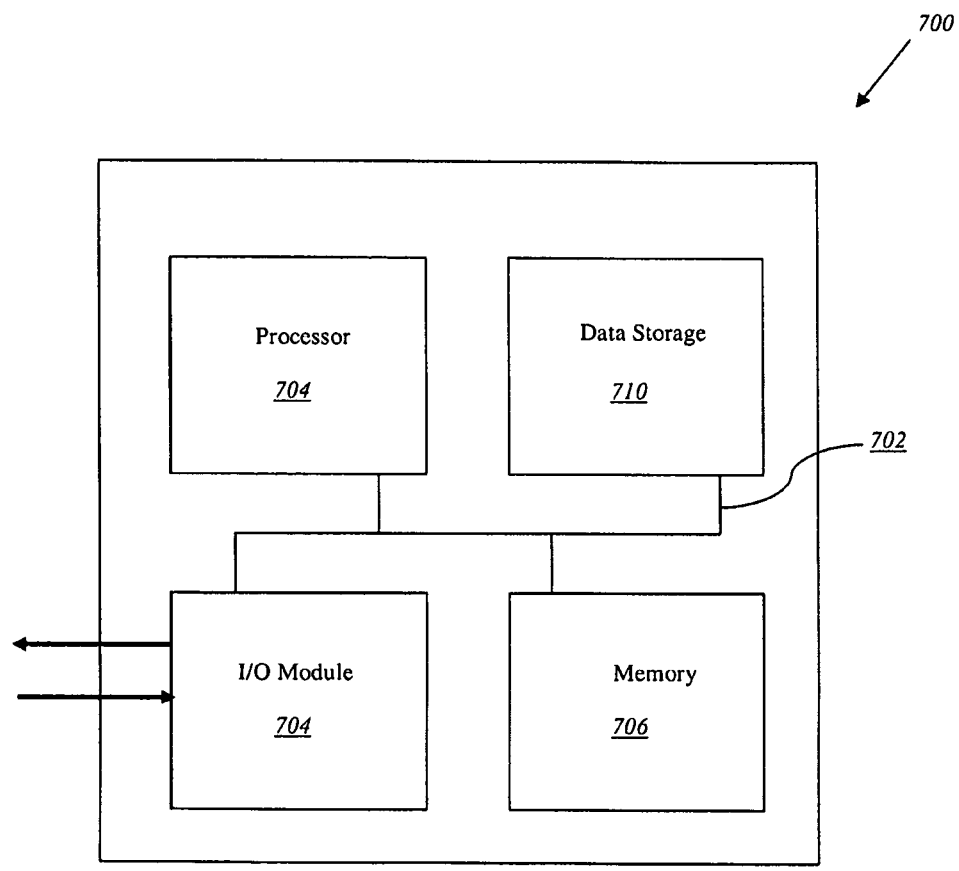
FIG. 7 is a block diagram that illustrates an exemplary computer system upon which certain features of vertical storage systems described herein may be implemented.

FIG. 7 is a block diagram that illustrates an exemplary computer system 700 upon which certain features of the storage system described herein may be implemented. Computer system 700 includes a bus 702 or other communication mechanism for communicating information, and a processor 704 coupled with bus 702 for processing information. Computer system 700 also includes a memory 706, such as a random access memory ("RAM") or other dynamic storage device, coupled to bus 702 for storing information and instructions to be executed by processor 704. Memory 706 may also be used for storing temporary variables or other intermediate information during execution of instructions by processor 704. Computer system 700 further includes a data storage device 710, such as a magnetic disk or optical disk, coupled to bus 702 for storing information and instructions.

Computer system 700 may be coupled via I/O module 708 to a display device (not illustrated), such as a cathode ray tube ("CRT") or liquid crystal display ("LCD") including a touch screen LCD display for displaying information to a computer user. An input device, such as, for example, a keyboard or a mouse may also be coupled to computer system 700 via I/O module 708 for communicating information and command selections to processor 704.

According to certain embodiments, certain aspects of user-authentication and inventory control functions described herein are performed by a computer system 700 in response to processor 704 executing one or more sequences of one or more instructions contained in memory 706. Processor 704 may be a microprocessor, a microcontroller, and a digital signal processor (DSP) capable of executing computer instructions. Such instructions may be read into memory 706 from another machine-readable medium, such as data storage device 710. Execution of the sequences of instructions contained in main memory 706 causes processor 704 to perform the process steps described herein. One or more processors in a multi-processing arrangement may also be employed to execute the sequences of instructions contained in memory 706. In alternative embodiments, hard-wired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 704 for execution. Such a medium may take many forms, including, but not limited to, non-volatile media, volatile media, and transmission media. Non-volatile media include, for example, optical or magnetic disks, such as data storage device 710. Volatile media include dynamic memory, such as memory 706. Transmission media include coaxial cables, copper wire, and fiber optics, including the wires that comprise bus 702. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A storage system for inventory control, the storage system comprising:
    a cabinet; and
    a vertical drawer movably coupled to the cabinet and configured to move between a first position and a second position,
    the vertical drawer having a plurality of vertically-stacked pockets, each vertically-stacked pocket configured to be separately openable for providing user access to contents of the vertically-stacked pocket.

2. The storage system of claim 1, wherein the vertical drawer is fully within the cabinet in the first position and is at least partially outside the cabinet in the second position.

3. The storage system of claim 1, wherein at least some of the pockets comprise electronically-controlled and individually-actuated locking devices to provide separately-controlled accesses to at least some of the pockets.

4. The storage system of claim 1, wherein the vertical door comprises a frame portion disposed above a row of vertically-stacked pockets, wherein the frame portion comprises electronically-controlled and individually-actuated locking devices to provide separately-controlled accesses to at least some of the pockets.

5. The storage system of claim 1 further comprising a memory arrangement configured to store information related to the contents of each vertically-stacked pocket.

6. The storage system of claim 5, wherein the memory arrangement includes a separate memory disposed in each vertically-stacked pocket.

7. The storage system of claim 5, wherein the memory arrangement is disposed separately from each vertically-stacked pocket and stores information related to the contents of the plurality of vertically-stacked pockets.

8. The storage system of claim 5 further comprising a processor in data communication with the memory arrangement, wherein the processor is configured to receive the content information and provide a controlled access to the contents.

9. The storage system of claim 8, wherein the processor is configured to receive the content information wirelessly from the memory arrangement.

10. The storage system of claim 8, wherein the controlled access comprises an electronic user-authentication.

11. The storage system of claim 10, wherein the electronic user-authentication comprises verification of biometric characteristics.

12. The storage system of claim 10, wherein the electronic user-authentication comprises verification of a password.

13. The storage system of claim 8, wherein the processor is further configured to provide an inventory control of the contents based on the content information.

14. The storage system of claim 13, wherein the inventory control comprises a maintenance of a record of contents of the plurality of pockets.

15. The storage system of claim 1, wherein at least some of the pockets are removable from the drawer.

16. The storage system of claim 15, wherein the drawer is reconfigurable by repositioning at least one of the removable pockets.

17. The storage system of claim 1, wherein the vertically-stacked pockets comprise at least one tilt-out bin.

18. The storage system of claim 1, wherein the storage system is a medication dispenser.

19. A storage system for inventory control, the storage system comprising:
 a cabinet; and
 a door movably coupled to the cabinet and configured to move between a closed position and an open position, the door having an inside surface and an outside surface,
 the door having a plurality of vertically-stacked pockets coupled to the inside surface of the door, each vertically-stacked pocket configured to be separately openable for providing user access to contents of the vertically-stacked pocket.

20. The storage system of claim 19 further comprising a plurality of electronically-controlled and individually-actuated locking devices to provide separately controlled accesses to at least some of the pockets.

21. The storage system of claim 20, wherein each of the locking devices is disposed inside each of the pockets.

22. The storage system of claim 20, wherein the locking devices are disposed inside a frame portion disposed above a row of vertically-stacked pockets.

23. A storage system for inventory control, the storage system comprising:
 a support structure; and
 a plurality of doors movably mounted to the support structure, each movably-mounted door configured to move between a first position and a second position, the door having an inside surface and an outside surface,
 the door having a plurality of vertically-stacked pockets coupled to at least one of the inside surface or the outside surface, each vertically-stacked pocket configured to be separately openable for providing user access to contents of the vertically-stacked pocket.

24. The storage system of claim 23, wherein the doors are pivotably-mounted to the support structure such that each door can be moved between the first and second positions in a rotational motion.

25. The storage system of claim 23, wherein the doors are slidably-mounted to the support structure such that each door can be moved between the first and second positions in a linear translational motion.

26. The storage system of claim 23 further comprising a plurality of electronically-controlled and individually-actuated locking devices to provide separately controlled accesses to at least some of the pockets.

27. A storage system for inventory control, the storage system comprising:
 a cabinet configured for wall mounting and having a plurality of vertically-stacked pockets; and
 a plurality of electronically-controlled and individually-actuated locking devices to provide separately controlled accesses to at least some of the pockets.

28. The storage system of claim 27, wherein each of the locking devices is disposed inside each of the pockets.

29. The storage system of claim 27, wherein the locking devices are disposed inside a frame portion disposed above a row of vertically-stacked pockets.

30. The storage system of claim 27, the wall-mounted cabinet further comprising a lockable door mounted to lockably enclose the plurality of vertically stacked pockets.

* * * * *